United States Patent [19]

Jerosch-Herold et al.

[11] Patent Number: 5,387,865
[45] Date of Patent: * Feb. 7, 1995

[54] PERMEABILITY DETERMINATION FROM NMR RELAXATION MEASUREMENTS FOR FLUIDS IN POROUS MEDIA

[75] Inventors: Michael Jerosch-Herold, High Bridge; Hans Thomann, Bedminster, both of N.J.

[73] Assignee: Exxon Research and Engineering Company, Florham Park, N.J.

[*] Notice: The portion of the term of this patent subsequent to Feb. 22, 2011 has been disclaimed.

[21] Appl. No.: 29,755

[22] Filed: Mar. 11, 1993

Related U.S. Application Data

[63] Continuation-in-part of Ser. No. 763,026, Sep. 20, 1991, Pat. No. 5,289,124.

[51] Int. Cl.$^6$ .............................................. G01R 33/20
[52] U.S. Cl. ..................................... 324/303; 324/300
[58] Field of Search .......................... 128/653.2, 653.5; 324/300, 303, 318, 307, 309

[56] References Cited

U.S. PATENT DOCUMENTS

| | | | |
|---|---|---|---|
| 4,719,423 | 1/1988 | Vinegar | 324/303 |
| 4,728,892 | 3/1988 | Vinegar | 324/309 |
| 4,933,638 | 6/1990 | Kenyon | 324/303 |
| 5,023,551 | 6/1991 | Kleinberg et al. | 324/303 |
| 5,055,788 | 10/1991 | Kleinberg et al. | 324/303 |

Primary Examiner—Louis Arana
Assistant Examiner—Raymond Y. Mah
Attorney, Agent, or Firm—Ronald D. Hantman

[57] ABSTRACT

The present invention is a method to rapidly determine the fluid-flow permeability of porous media with nuclear magnetic resonance (NMR). The method can be applied to measurements of permeability in fluid-saturated earth formations using NMR logging tools.

21 Claims, 10 Drawing Sheets $T_2$ FROM FIT OF m (t) TO
$\exp[-(t/T_2)\beta]$ $T_2$ = 37.833
$\beta_2$ = 0.64245

$T_2$ FROM FIT OF m (t) TO
$\exp[-(t/T_2)\beta]$

Rf PULSES:

RECEIVER CHANNEL:

PERMEABILITY DETERMINATION FROM NMR RELAXATION MEASUREMENTS FOR FLUIDS IN POROUS MEDIA

CROSS REFERENCE TO RELATED APPLICATION

This is a continuation-in-part of U.S. Ser. No. 763,026 filed Sept. 20, 1991 now U.S. Pat. No. 5,289,124.

BACKGROUND OF THE INVENTION

The present invention relates to a method for determining the fluid flow permeability of porous media. In particular, the present invention relates to measuring the permeability by nuclear magnetic resonance (NMR) using the $T_2$ relaxation time for the decay of the transverse magnetization of fluids saturating the medium under investigation.

The properties of fluid in porous media are of great relevance in many fields of science and engineering. There are numerous measurements which bear some importance on characterizing fluid properties in confined geometries like sandstone rocks. We list here a few: porosity, fluid flow permeability (both dc and ac), electrical conductivity, wettability, etc. Quantities like porosity and fluid flow permeability in porous rocks are of great relevance for determining, the producibility of petroleum reservoirs.

For porous media it has become customary to speak of the solid material which forms the "backbone" as the matrix and its complement as the pore space. Porosity is defined as the ratio of pore space volume inside the porous material to the total volume of the porous medium. Permeability is a measure for the ability of porous materials like e.g. porous rocks to permit fluid flow through the pore space. It generally increases with porosity, but also depends on other parameters of the rocks as e.g. the specific surface area of the pore space, the pore size distribution and the pore shape. The fluid flow permeability can vary by about 8 orders of magnitude in loose sediments and sedimentary rocks. It has the dimension of area and is defined by Darcy's law which relates the rate of fluid flow to the pressure differential between two parallel planes for inflow and outflow. The fluid flow permeability is measured in the laboratory by fitting sleeves to core samples which are often cylindrically shaped. The top and bottom of the core samples are connected to fluid inlets and outlets and a known pressure difference is applied across the sample. The fluid flow rate is measured for a set of different pressure gradient. Liquids or gases can be used as flowing medium, although the measurement using a liquid is generally easier as in most cases the liquid can be considered incompressible. The laboratory procedure therefore requires first to drill core plugs from core samples, which have to be cleaned with various solvents. In contrast the method of the present invention can be carried out with a nuclear magnetic resonance logging tool to measure in situ the transverse relaxation time of the fluids saturating an earth formation to accurately predict the fluid flow permeability of the earth formation.

Nuclear magnetic resonance (NMR) has been employed for some time to study fluids permeating the pore space of porous media [see J. R. Banavar and L. M. Schwartz, "Molecular Dynamics in Restricted Geometries", chapter 10, edited by J. Klafter and J. M. Drake, J. Wiley (1989)]. The fluid supplies the probe particles which diffuse in the pore space. Since the classic paper by Brownstein and Tarr (BT) [see K. R. Brownstein and C. E. Tarr, *Physical Review* A, 19, 2446(1979)] it has been realized that nuclear spin relaxation can provide information about the pore space geometry. BT discussed the case of $T_1$ and $T_2$ relaxation in an isolated pore where the nuclear spins are relaxed by collisions with the pore walls. The interpretation of $T_1$ measurements with this model for fluids in porous media can present several problems. In the limit where the nuclear spins diffuse at a fast rate to the pore surface and the surface relaxation is in comparison relatively slow, the averaged relaxation curve can be related to the pore size probability distribution. In this so called fast diffusion limit where the lowest order relaxation mode dominates one still has to assume that the surface relaxation strength is uniform and the pores are isolated to relate the distribution of relaxation times uniquely to the pore size distribution. It is conceivable to have porous samples with the same pore size geometry but different levels of paramagnetic impurities which influence the surface relaxation velocity while the fluid flow permeability would remain unchanged. To obtain a reliable estimate of the fluid flow permeability with NMR one therefore has to perform an experiment which directly probes fluid transport in the porous medium like for example the diffusion of fluid molecules in the pore space. For $T_1$ measurements the nuclear spin relaxation depends on the rate at which magnetization is carried to the surface but also on the surface relaxation velocity $\rho$. As the surface relaxation strength $\rho$ has no bearing on permeability one can therefore hope to correlate $T_1$ and the fluid flow permeability only for classes of materials with similar surface relaxation properties.

There is an increasing interest in applying NMR in well-bore environments to determine the properties of fluid carrying earth formations [see P. N. Sen, C. Straley, W. E. Kenyon and M. S. Whittingham, *Geophysics*, 55, 61–69(1990)]. This interest has been spurred by the introduction of a new generation of NMR logging tools by NUMAR [see M. N. Miller, A. Paltiel, M. E. Gillen, J. Granot and J. C. Brouton, Society of Petroleum Engineers, SPE 20561, 321(1990)], which are already being used in the field. The new NMR logging tools are very well fitted to carry out the physical measurements required for our method of invention.

In the present invention, a measurement of the transverse relaxation time $T_2$ for fluids in porous media is used to determine the permeability of the medium by taking advantage of magnetic field inhomogeneities across pores. For strong magnetic fields and in the fast diffusion limit the relaxation is determined to first order by the transport of magnetization through the pore space and not the surface relaxation velocity. It will be shown that it is possible to correlate $T_2$ to a length characteristic of the pore space geometry which can also be determined independently from mercury injection experiments and thereby relate $T_2$ to the fluid flow permeability. It is also feasible to study the degree to which the diffusion of fluid molecules is restricted by the pore space geometry. $T_2$ for fluids in porous media is in general orders of magnitude shorter than $T_1$ in marked contrast to the situation for bulk fluids. The main mechanism for $T_2$ relaxation of the fluid spins in strong magnetic fields is due to the internal random magnetic field gradients generated by the difference in magnetic susceptibility for the fluid filling the pore space and the material making up the matrix of the porous medium. At low fields surface relaxation can not be be neglected but the $\tau$ dependence of $T_2(\tau)$ is still primarily due to diffusion in the internal magnetic field gradients. Surface relaxation will under standard experimental conditions not lead to a $\tau$ dependence of $T_2$ in a CPMG experiment. This is confirmed by recent experimental results at low field with an NMR logging tool[see M. N. Miller, A. Paltiel, M. E. Gillen, J. Granot and J. C. Brouton, Society of Petroleum Engineers, SPE 20561, 321(1990)]. The spatial dependence of the internal gradients is determined by the pore space geometry and pore size distribution. The internal gradients in turn determine the rate at which the spins diffusing through the pore space loose their phase memory. The loss of phase memory can be monitored with a multi spin-echo pulse sequence like the Carr-Purcell-Meiboom-Gill (CPMG) pulse sequence [see S. Meiboom and D. Gill, *Rev. Sci. Instr.*, 29, 688 (1958)].

The phenomenon of spin echoes essential to the present invention was first discovered in NMR by Erwin Hahn [see E. L. Hahn, *Phys. Rev.*, 77, 297 (1950)]. In an inhomogeneous magnetic field nuclear spins will precess at a Larmor frequency, $\nu_L$, determined by the local field. After an initial radiofrequency pulse which tips the spins into a plane transverse to the direction of the applied static magnetic field the spins are all in phase and the sum of the total transverse magnetization is at the maximum possible value. Due to the spread in precession frequencies the spins will dephase and the macroscopic magnetization measured with the NMR instrument will decay. It is useful to remember here that the macroscopic magnetization is a vector sum of the magnetic moments of the spins which vanishes when the phases of the magnetic moments are random. One can reverse the dephasing process by applying a 180 degree pulse a time $\tau/2$ after the initial radio-frequency pulse which tipped the nuclear spins into the transverse plane. Immediately after this pulse a spin which precesses at a faster frequency than the average lags behind by an angle which is exactly the same angle by which it was ahead of the average immediately before the 180 degree pulse. Similarly spins precessing at a frequency slower than the average are now ahead. A time $\tau/2$ after the 180 degree pulse the spins will be again be in phase and one can observe a spin-echo. Spins diffusing will be subject to different local fields between the time the first pulse was applied and the detection of the spin echo. As their Larmor frequency is not constant the refocusing of magnetization will be incomplete and the echo will be attenuated. The degree of attenuation depends on the displacement and field inhomogeneity. This attenuation can be used to measure diffusion constants in fluids and to probe the diffusion of fluid spins in the pore space of porous media.

SUMMARY OF THE INVENTION

The present invention provides a method for determining the permeability of porous media saturated with a liquid using nuclear magnetic resonance (NMR). The steps of the method include: (a) applying a radiofrequency pulse sequence which after an initial pulse generates successive spin echoes with a train of radio frequency pulses spaced apart by a time interval of length $\tau$ wherein all pulses have a carrier frequency corresponding to the Larmor frequency of the fluid spins filling the pore space of the medium for which the fluid flow permeability is to be determined; (b) measuring the decay of the transverse magnetization at each of the successive regularly spaced midpoints between the 180 degree pulses where the midpoints coincide with the peak of the spin echoes; (c) repeating steps a and b at least one more time wherein each repeat of step (a) uses said radio frequency pulse train with a different value of the pulse spacing $\tau$; (d) determining the transverse relaxation time $T_2(\tau)$, from the transverse magnetization decay for each value of $\tau$ and determining one of a prefactor $\Delta$ or a restricted diffusion length $l_{nmr}$ from said $T_2(\tau)$; (e) measuring the porosity of said porous media; (f) determining the permeability of said media from the porosity and either a prefactor $\Delta$ or a restricted diffusion length $l_{nmr}$ from said $T_2(\tau)$.

In a preferred embodiment the method is performed as a down-hole wellbore measurement to swiftly and accurately determine the fluid-producing potential of an earth formation using a magnetic resonance logging system which employs static and radio-frequency magnetic fields to perform the spin-echo CPMG pulse experiment in a wellbore environment.

DESCRIPTION OF THE PREFERRED EMBODIMENT

Figure 1A:
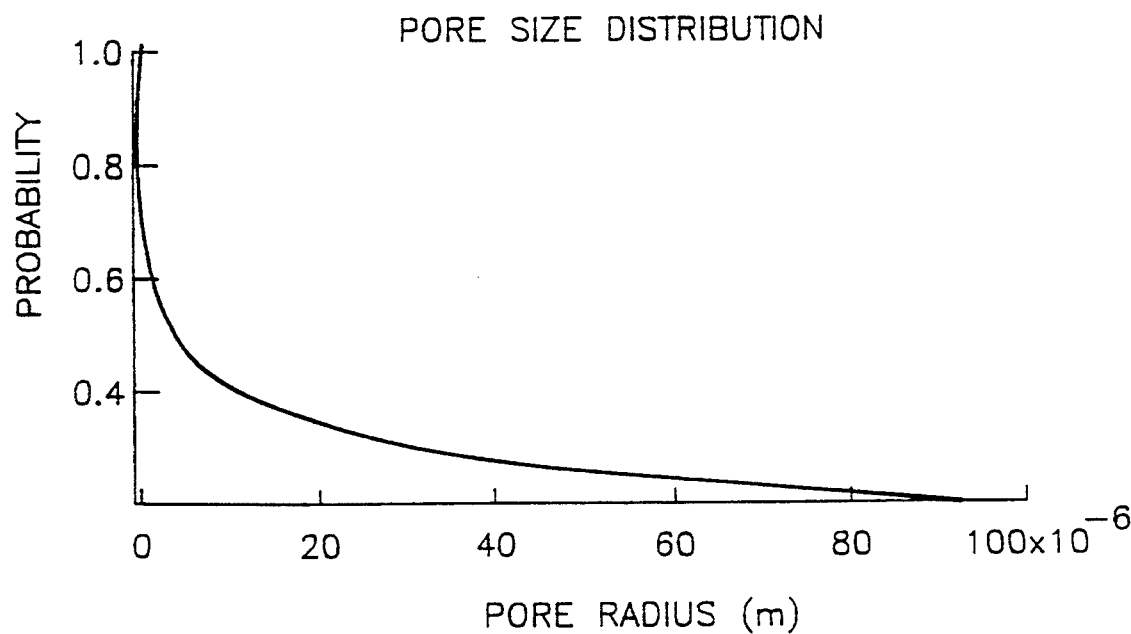
FIG. 1a shows pore size distribution calculated with equation 11.

The present invention is a method to determine the permeability of porous media using pulsed nuclear magnetic resonance. This method uses the relaxation decay of the transverse component of the magnetization ($T_2$ relaxation) measured with the Carr-Purcell- Meiboom-Gill (CPMG) pulse sequence.

It can be shown (see below) that the magnetization as a function of time, t is described by a stretched exponential decay function of the form:

$$m(t) \propto \exp[-(t/T_2)^{62\ 2}], \tag{1}$$

where $\beta_2$ is the stretch exponent. A nonlinear least squares fit of the measured values of magnetization m(t) to the stretched exponential function determines the relaxation time $T_2$ and the stretch exponent, $\beta_2$. If the pulse spacing, $\tau$, is changed in incremental steps, a set of stretched exponential curves is produced yielding different values for $T_2(\tau)$. For the case of free diffusion, the pore size distribution introduces a spectrum of $T_2$ decay values because the internal magnetic field gradient is related to the pore size. The analysis of the transverse magnetization decay in this case yields an effective $T_2$, which is a weighted average over the range of $T_2$ values. In this case a characteristic length can be determined from the prefactor of the functional form that describes the $\tau$ dependence of $T_2(\tau)$. When $T_2$ is only measured for a limited range of $\tau$ values this prefactor is dominated by the pore size distribution and is not very sensitive to the exact functional form of $T_2(\tau)$. A characteristic length, $\Delta$, is derived from this prefactor.

$$T_2(\tau) \propto \Delta/F(\tau) \qquad (2)$$

where $F(\tau)$ is a fitting function which reproduces the $\tau$ dependence of $T_2$. Specific forms for $F(\tau)$ are discussed in the section on Theoretical Background.

For a sufficiently wide range of $\tau$ values, the exact functional form of $T_2(\tau)$ is determined by the cross-over from free to restricted diffusion. For a given range of $\tau$ values, this cross-over is also dependent on the pore size distribution. Analysis of the functional form of $T_2(\tau)$ in the region of this cross-over yields a characteristic length, $l_{nmr}$, according to:

$$T_2^{-1}(\tau) = \frac{(\gamma G l_{nmr})^2}{12} \tau[1 - \exp(-D_o\tau/l_{nmr}^2)]. \qquad (3)$$

In either case, the characteristic lengths, $\Delta$ or $l_{nmr}$, derived from the decay of $T_2(\tau)$ with $\tau$, are a measure of the fluid flow permeability. With $l_{nmr}$ the fluid flow permeability is determined with $$k \propto l_{nmr}{}^n \phi^m \qquad (4)$$

If a prefactor $\Delta$ has been determined from $T_2(\tau)$ the fluid flow permeability is determined with:

$$k \propto \Delta^n \phi^m \qquad (5)$$

If $T_2(\tau)$ is a simple exponential then the prefactor $\Delta$ and the extrapolated value of $T_2(\tau)$ are related by $T_2(\tau\to 0) \propto \Delta$. The value of $T_2$ extrapolated to $\tau=0$ combined with the porosity, $\phi$, of the material gives the permeability, k, of the porous medium according to (see FIG. 9):

$$k \propto [T_2(\tau\to 0)]^n \phi^m. \qquad (6)$$

The permeability relations 4, 5 and 6 follow from the relations: $k \propto l_c^2 \phi^2$ and $\Delta \propto l_{nmr} \propto l_c$ and $T_2(\tau\to 0) \propto \Delta$. The proportionality constants in these permeability relationships 4, 5 and 6 can be determined from a calibration experiment with a porous material of known porosity and permeability. The exponents n and m may vary depending on which of the above relations 4, 5 and 6 is used to determine the permeability. The values of n and m are not necessarily the same for each of the relationships. The porosity is determined by first running an NMR experiment with a water jacket which surrounds the radiofrequency probe (e.g. of the NMR logging tool) and therefore calibrates the NMR signal for 100% porosity. To prevent the interference from local radio signals one can enclose the probe and water jacket in a Faraday cage. As the NMR signal is directly proportional to the number of hydrogen nuclei in the sensitive volume of the probe it will scale linearly to lower porosities. Only the contribution from liquid phases or non-adsorbed fluid will be recorded if the dead time of the instrument is set accordingly. The temperature of the fluid in the sensitive volume is of secondary influence. In a bore hole environment this varies with depth and can be compensated for by measuring the bottom temperature and temperature gradient. The NMR signal amplitude changes as a function of temperature as 1/T.

THEORETICAL BACKGROUND

The magnetization of the fluid spins diffusing in the pore space satisfies the following modified Bloch equation:

$$\frac{\partial M}{\partial t} = D\nabla^2 M - \frac{M}{T_b}. \qquad (7)$$

$T_b$ is the bulk relaxation rate of the fluid in the pore space and D is the diffusion constant which is on the order of $2\times 10^9 [m^2/sec]$ for water at room temperature. The boundary condition is:

$$D\tilde{n}\cdot\nabla M + \rho M|_{surface} = 0. \qquad (8)$$

where $\rho$ is the surface relaxation velocity, which has units of length over time and can be thought of as the relaxation rate at the surface multiplied by the thickness of the layer of fluid spins relaxing near the surface. The bulk relaxation rate can always be factored out of the solution.

$$M(r,t) = m(r,t)\exp(-t/T_b) \qquad (9)$$

The Bloch equation becomes:

$$\frac{\partial m}{\partial t} = D\nabla^2 m \qquad (10)$$

Brownstein and Tarr [K. R. Brownstein and C. E. Tarr, *Physical Review A*, 19, 2446-2453 (1979)] expressed the general solution as a sum of normal modes:

$$m(t) = m(\theta) \sum_{n=0}^{\infty} I_n \exp -t/T_n \qquad (11)$$

$$T_0 >> T_1 >> T_2 \ldots$$

Two limiting cases can be considered for the magnetization decay which are characterized by decay constants $\tau_c$:

$$\tau_c = \begin{cases} r^2/D & \text{diffusion limited: } \rho r/D >> 1 \\ r/\rho & \text{fast diffusion: } \rho r/D << 1 \end{cases} \qquad (12)$$

In the fast diffusion case the magnetization is approximately uniform across an isolated pore and only the lowest mode in the above eigenmode expansion contributes significantly to the magnetization decay. In this limit, $\rho r/D \ll 1$, and when the pores are approximately isolated (narrow throat limit) one obtains for m(t):

$$m(t) = \exp\left(-\frac{\rho S_p}{V_p} t\right) \qquad (13)$$

$S_p$ and $V_p$ are the surface area and the volume of a pore and $V_p/S_p \approx r$. For a pore size distribution the relaxation is described by:

$$\tilde{m}(t) = \int_{r_c}^{\infty} P(r) r^3 \exp\left(-\frac{\rho}{r} t\right) dr. \qquad (14)$$

$r_c$ is a lower cut-off on the pore size distribution. Thompson et al [see A. H. Thompson, S. W. Sinton, S. L. Huff, A. J. Katz, R. A. Raschke and G. A. Gist, *Journal of Applied Physics*, 65, 3259 (1989)] found that the pore size distribution of many porous rocks is well represented by the following class of functions:

$$P(r)dr \propto \exp[-(r/\Delta)^{\beta/(1-\beta)}] dr \qquad (15)$$

and where $\Delta$ is a measure of the width of the pore size distribution and $\beta$ lies between 0 and 1. A $\beta$ value of 2/3 will yield a Guassian pore size distribution. This type of pore size distribution will lead to a stretched exponential decay in the fast diffusion limit:

$$m(t) \propto \exp[-(t/T_{1,2})^{\beta 1.2}]. \qquad (16)$$

This result is obtained by using the saddle point method on the integral in equation 14, i.e., we determine the pore size radius for which the exponent of the integrand goes through a maximum as a function of pore radius r.

Equation 16 is of a form observed experimentally for $T_1$ and $T_2$ magnetization decays for fluids in porous media for a broad set of experimental conditions, although it was derived for the case of surface induced relaxation. We wish to arrive at an expression which explicity accounts for the contribution to the $T_2$ decay from diffusion of fluid spins in porous media in the presence of internal magnetic field gradients. The magnetic field gradients lead to dephasing of the nuclear spins which can only be partially compensated with a spin-echo sequence as they diffuse. As a starting point we use an expression derived by Robertson and Neuman and experimentally confirmed by Wayne and Cotts for the decay of the transverse magnetization in the presence of a uniform gradient G [see B. Robertson *Physical Review*, 151(1), 273 (1966), R. C. Wayne and R. M. Cotts, *Physical Review*, 151(1), 263 (1966), C. H. Neuman, *The Journal of Chemical Physics*, 60 (11), 4508 (1974)]. Neuman produced expressions for the case where the spins are assumed to diffuse in a bounded medium of spherical geometry and the Carr-Purcell spin-echo sequence with spacing of the $\pi$ pulses given by $\tau$ is being used:

$$m(t) = m_0 \exp\left(-\frac{2\gamma^2 G^2 r^4 t}{D} \times \right. \qquad (17)$$

$$\left. \sum_{i=1}^{\infty} \frac{1}{\alpha_i^4(\alpha_i^2 - 2)} \left(1 - \frac{3 - 4e^{-\alpha_i^2\theta/2} + e^{-\alpha_i^2\theta}}{\alpha_i^2\theta}\right)\right)$$

$\theta = 2\tau D/r^2$ and the $\alpha$ are determined from $\tan \alpha_i = -2\alpha_i/(2-\alpha_i^2)$ whose solutions asymptotically approach: $\alpha_i = i \cdot \pi$. For small $\pi$ the above expression agrees with the well-known expression for transverse relaxation of spins due to unrestricted diffusion in a uniform gradient:

$$m(t) = m_0 \exp[-\gamma^2 G^2 \tau^2 Dt/12]. \qquad (18)$$

Since porous media are characterized by a distribution of pore sizes the internal gradients should be parametrized in terms of pore size length. To this end we make the reasonable assumption that the magnetic field gradient across a pore of radius r is inversely proportional to the pore radius:

$$G = \mu_0 H_0 \Delta \chi / r \qquad (19)$$

$\Delta \chi$ is the susceptibility difference, $\mu_o$ the magnetic permeability of vacuum and $H_o$ the magnetic field strength. This means that under this model the gradient is uniform over individual pores but varies from pore to pore. The contribution of the spins in each pore has to be weighted by the volume of the pore. For a pore size distribution we must average the magnetization decay, m(t), over the pore size distribution in a fashion similar to the example in equation 14. We therefore arrive at the following expression for the contribution to the transverse magnetization of the spins diffusing in random internal gradient fields:

$$m(t) \propto \int_0^{\infty} dr P(r) r^3 \times \qquad (20)$$

$$\exp\left(-\frac{2\gamma(\mu_0 H_0 \Delta \chi^2 a^2 t}{D} \sum_{i=1}^{\infty} \frac{1}{\alpha_i^4(\alpha_i^2 - 2)} \left(1 - \right.\right.$$

$$\left.\left. \frac{3 - 4e^{-\alpha_i^2\theta/2} + e^{-\alpha_i^2\theta}}{\alpha_i^2\theta/2}\right)\right) \times \exp[-\rho t/r]$$

where the last exponential explicitly accounts for the possibility of surface relaxation. This expression is the basis for numerical calculations performed for a series of pore size distributions. This expression was also previously, independently derived by Kleinberg and Horsfield [see R. L. Kleinberg and M. A. Horsfield, *Journal of Magnetic Resonance*, 88, 9–19 (1990)]. We numerically calculated the CPMG echo decay curve with the sum over the roots $\alpha_i$ being approximated up to the 20th term. The pore size distribution is of the form shown in Equation 15. The simulations were carried out in the same manner as the experiment. The CPMG decays were calculated for a set of values of $\tau$. We observe that the calculated magnetization decays are well described by stretched exponential functions. This suggests that equation 16 applies to a broader class of relaxation decays than suggested by the derivation which only considered surface induced relaxation. Indeed the numerical results show that the decay of the magnetization due to diffusion in the presence of random magnetic field gradients and averaged over a pore size distribution also leads to stretched exponential decays.

Figure 1B:
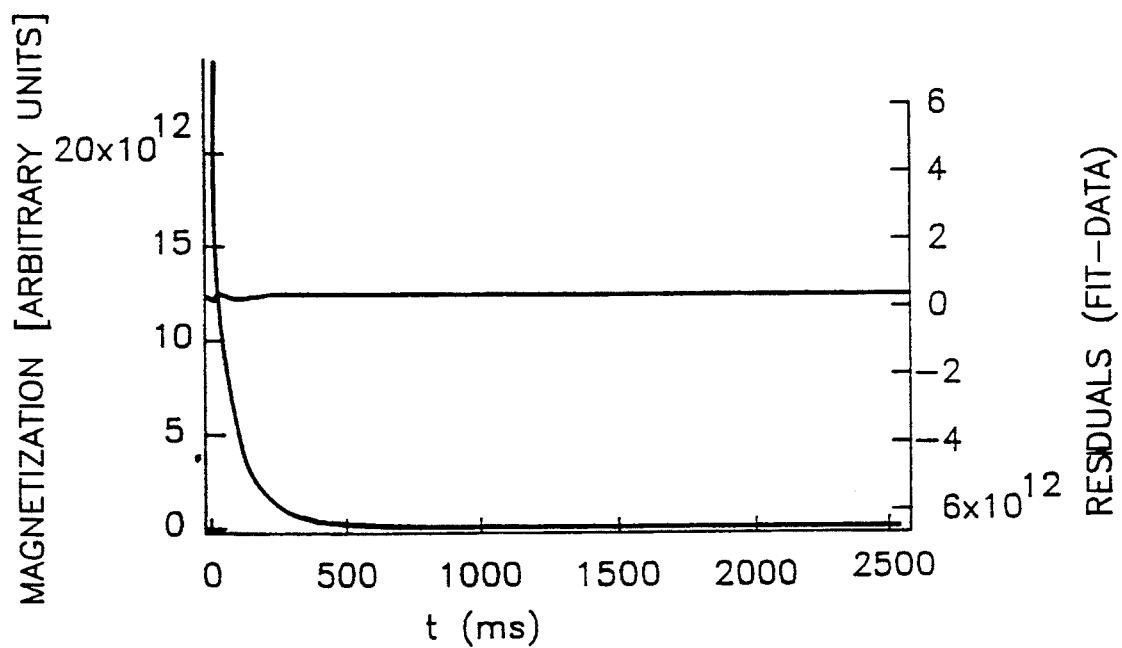
FIG. 1b shows the numberically evaluated CPMG decay for a certain $\tau$ value and the pore size distribution shown in (1a)
Figure 1C:
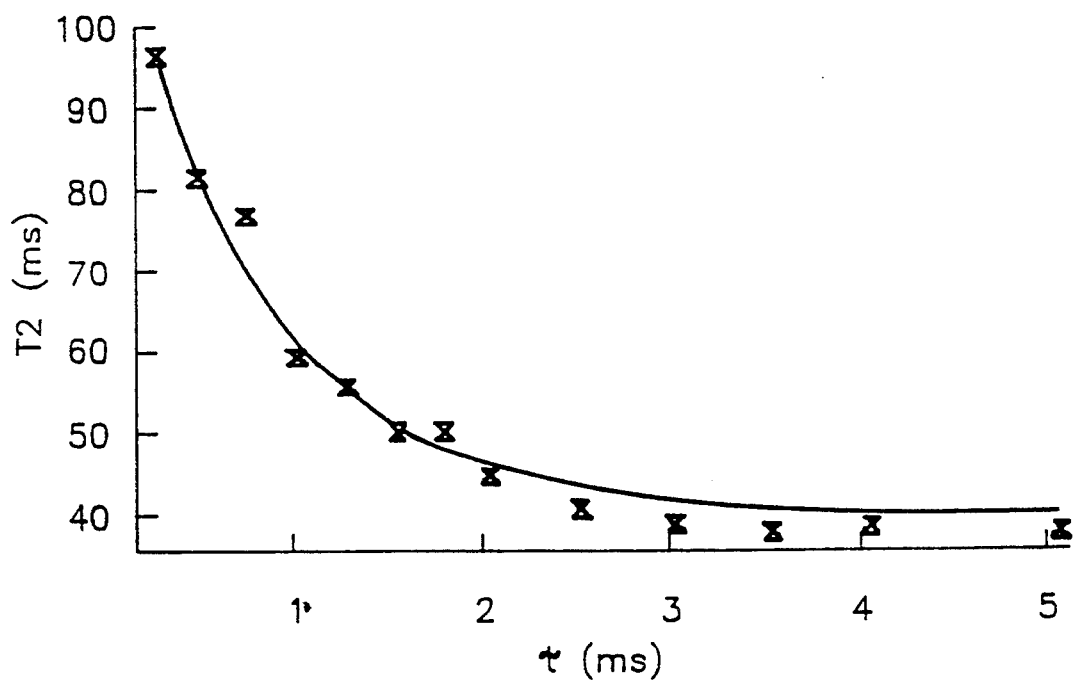
FIG. 1c shows the $T_2$ values calculated from computer simulated CPMG decays for the same pore size distribution.

FIG. 1a shows the pore size distribution calculated from equation 15 for typical values of $\Delta$ and $\beta$. FIG. 1b shows the magnetization decay calculated for the pore size distribution of 1a from equation 20. This calculation was repeated for several values of $\tau$ and the nonlinear least squares fits to the stretched exponential function yield values for $T_2$ and $\beta_2$. FIG. 1c shows the $T_2$ values thus obtained for a set of $\tau$ values.

Restricted diffusion can be expected at longer values of $\tau$. The diffusion dynamics were therefore studied by systematically varying the parmameter $\tau$ in the CPMG sequence. The crossover from free to restricted diffusion will then be evident in the dependence of both $T_2$ and $\beta_2$ on the diffusion time set by $\tau$. CPMG experiments were repeated for a series of $\tau$ values. Values for $T_2$ and $\beta_2$ were obtained by non-linear least squares fits to a stretched exponential function for each coherence decay. For free diffusion is a linear gradient G the CPMG $T_2^{-1}$ should be $\propto (\gamma G)^2 D\tau^2$, where D is the diffusion constant. For restricted diffusion D becomes effectively time dependent. To explain the $\tau$ dependence of $T_2$ we use a model which interpolates between the limits of free diffusion considered above and restricted diffusion at long $\tau$. The cross-over from unrestricted to restricted diffusion is well characterized by:

$$D_{eff} = l_{nmr}^2 [1 - \exp(-D_o\tau/l_{nmr}^2)]/\tau, \tag{21}$$

a result which was derived first in a pioneering paper by Stejskal on NMR measurements of restricted diffusion [E. O. Stejskal, *Journal of Chemical Physics*, 43, 3597–3603 (1965)]. $l_{nmr}$ should be on the order of $V_p/S_p$, the volume-to-surface ratio of a pore. This gives a $\tau$ dependence for $T_2$ of the form:

$$T_2^{-1}(\tau) = \frac{(\gamma G l_{nmr})^2}{12} \tau [1 - \exp(-D_o\tau/l_{nmr}^2)] \tag{22}$$

This approximation for $T_2(\tau)$ leads to the correct limiting behavior for $\tau \to 0$. The experimental data points for $T_2(\tau)^{-1}$ fit well to the above equation. We observe that for typical parameters. $4D_o\tau/l_{nmr}^2 \ll 1$. A power series expansion of equation 22 is therefore adequate as an approximation for $T_2(\tau)$:

$$T_2^{-1}(\tau) \approx \frac{(\gamma G)^2}{12} D_o \left[ \tau^2 - \frac{D_o\tau^3}{l_{nmr}^2} \right]. \tag{23}$$

Figure 2:
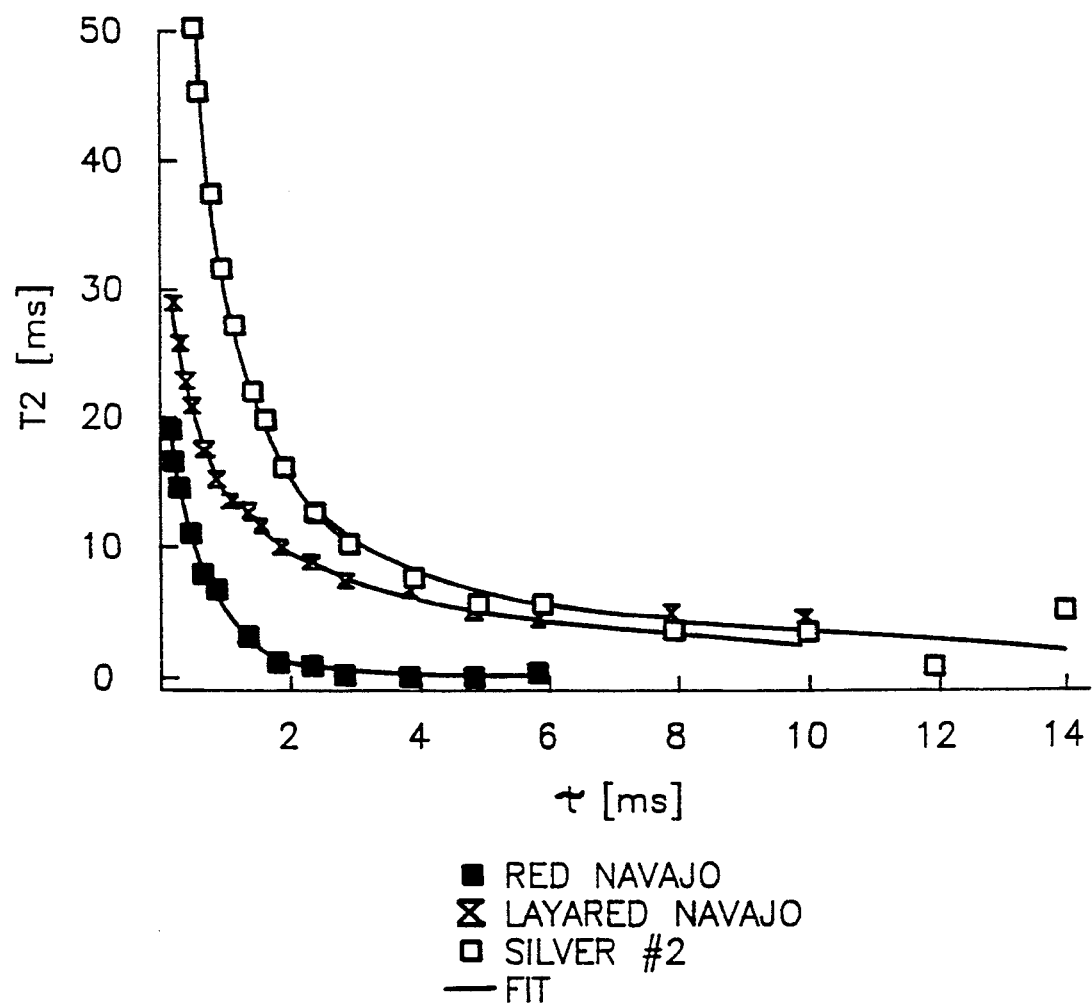
FIG. 2 shows a fit of $T_2$ ($\tau$) for a restricted diffusion model.
Figure 3:
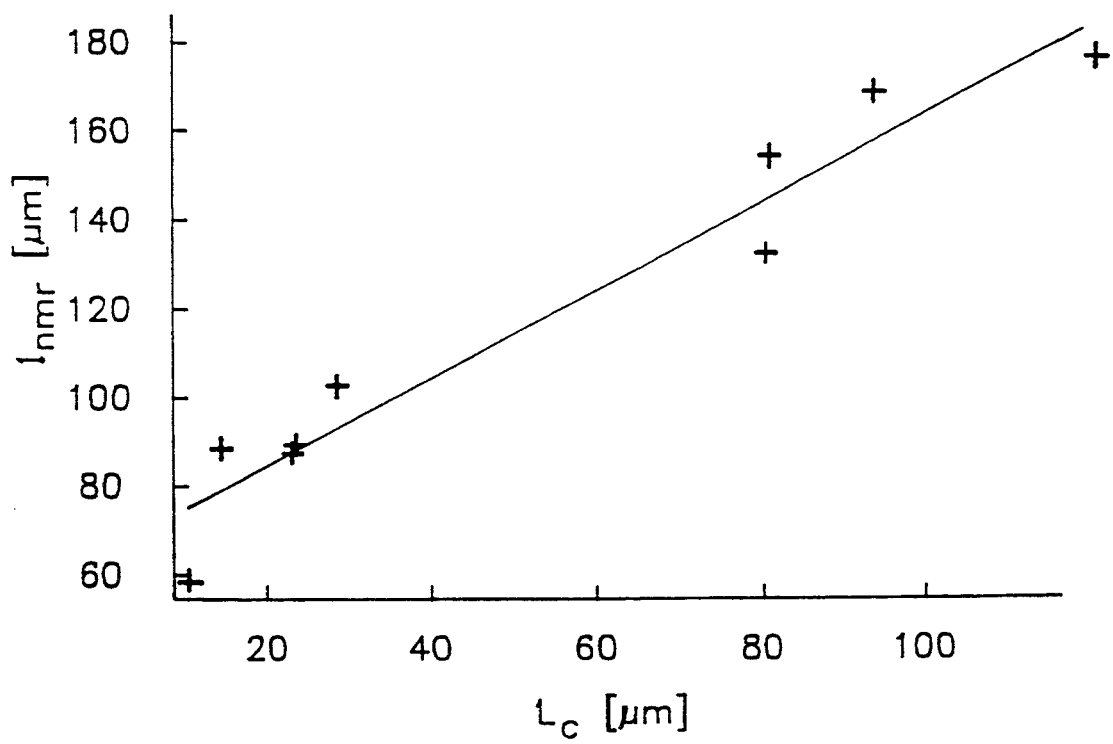
FIG. 3 shows a plot of the restricted diffusion length $l_{nmr}$ versus $l_c$ obtained from mercury injection experiments.

The fit of equation 23 or 22 to the experimental $T_2(\tau)$ data for several sandstone rocks are shown in FIG. 2. The fits to the experimental data yield coefficients for the two terms in the expression for $T_2(\tau)^{-1}$ of opposite sign as suggested by equation 23. The resulting values for $l_{nmr}$ are seen in FIG. 3 to correlate with a quantity $l_c$ derived from mercury injection. $l_c$ provides an estimate of the fluid flow permeability [see A. H. Thompson, S. W. Sinton, S. L. Huff, A. J. Katz, R. A. Raschke and G. A. Gist, *J. Appl. Phys.*, 65(8), 3259 (1989)]. Therefore since $l_c$ is proportional to $l_{nmr}$, $l_{nmr}$ provides an estimate of the fluid flow permeability. Mercury injection data indicate that the exponents n and m in equation 4 should be on the order of 2.0.

Equation 22 is one approximation to the crossover from free to restricted diffusion and other expressions have been proposed in the literature. All have in common that they provide a characteristic length $l_{nmr}$ which is of relevance to determine the transport properties of the porous medium. The restricted diffusion analysis presented above is therefore not confined to the use of equation 22 but can be used for a variety of models describing the crossover from free to restricted diffusion. An example of an alternative model is equation 20 (used for numerical calculations), where the sum in the exponent can be used to define an effective diffusion coefficient. In each case the crossover from free to restricted diffusion is probed by measuring the $\tau$ dependence of $T_2(\tau)$ as outlined in this invention.

PREFACTOR ANALYSIS

In actual practice the ability to determine the exact functional form which describes the $\tau$ dependence of $T_2(\tau)$ is limited by the time available for signal collection. This limits both the range of $\tau$ values which can be measured and the signal-to-noise ratio of the data. However in each case there is a characteristic length which determines the dominant contribution to $T_2(\tau)$. This length is related to the mean life time $<t>$ for the magnetization decay. The mean life time is defined by [see D. J. Wilkinson, D. L. Johnson and L. M. Schwartz", *Phys. Rev. B*, 44, 4960–4973 (1991)]:

$$<t> = \frac{1}{m(t=0)} \int_0^\infty m(t)dt \tag{24}$$

For stretched exponential decays the mean life time and $T_2$ from a nonlinear least squares fit to a stretched exponential are simply related: $<t> = T_2\Gamma(1/\beta_2)$ and for the range of $\beta_2$ values typical for magnetization decays in rocks the dependence of the mean life time on $\beta_2$ is weak. Using the approximation of free diffusion and with the assumption that the magnetic field gradient is inversely proportional to the pore radius the mean life time for the transverse magnetization decay is given by:

$$<t> = \tag{25}$$

$$\int_{t=0}^\infty \int_{r_c}^\infty P(r)r^3 \exp[-\delta\omega^2\tau^2 tD/12r^2]drdt / \int_{r_c}^\infty P(r)r^3 dr$$

where $\delta\omega = \gamma Gr \approx \gamma\Delta\chi H_o$. The free diffusion expression is a good approximation when $T_2$ is measured only for a limited set of short $\tau$ values. Using equation 15 for the pore size distribution and a change of variable $((r/\Delta)^{\beta/(1-\beta)} = x)$, the mean lifetime is given by:

$$<t> = \frac{\Delta}{\delta\omega^2 D\tau^2} \Gamma\left(\frac{4+2\beta}{\beta}\right)\left[1 - \right. \tag{26}$$

$$\left. \Gamma\left(\frac{4+2\beta}{\beta}, (r_c/\Delta)^{\beta/(1-\beta)}\right)\right] /$$

$$\Gamma\left(\frac{2+2\beta}{\beta}\right)\left[1 - \Gamma\left(\frac{2+2\beta}{\beta}, (r_c/\Delta)^{\beta/(1-\beta)}\right)\right]$$

Significantly the mean life time and therefore also $T_2$ are directly proportional to $\Delta$ and only weakly dependent on $\beta$ and $r_c/\Delta$ for typical values of these two parameters. This relation between $T_2$ and $\Delta$ is a consequence of the pore size distribution. This result remains unchanged if we generalize the expression for the mean life time to include a different $\tau$ dependence for $T_2(\tau)$. This is evident by substituting a general functional dependence $T_2 \propto F(\tau)$ in place of the $T_2 \propto \tau^{-2}$ in the above integral.

$$<t> = \int_{t=0}^{\infty} \int_{r_c}^{\infty} P(r)r^3 \exp[-\delta\omega^2 F(\tau D/r^2)t] dr dt / \int_{r_c}^{\infty} P(r)r^3 dr \quad (27)$$

Figure 4:
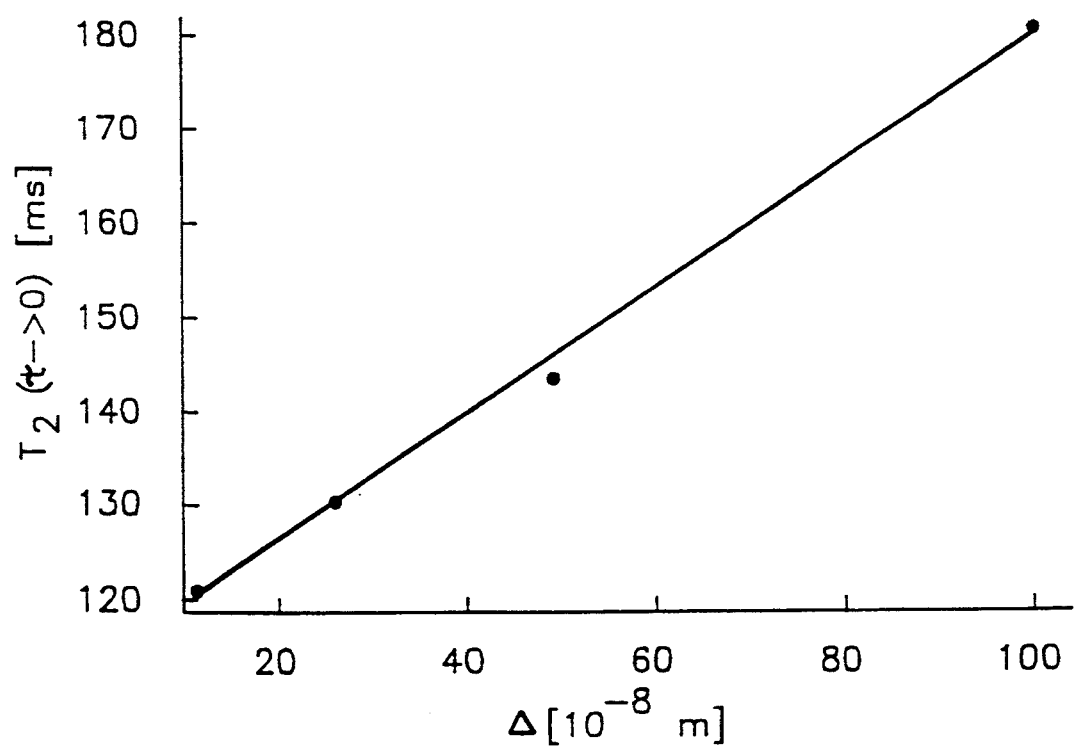
FIG. 4 shows the values of $T_2(\tau \rightarrow 0)$ obtained from numerical calculations for a set of pore size distributions versus the width $\Delta$ of the pore size distribution.

Empirically we have observed that at a magnetic field of 7T and for the range of experimental $\tau$ values used, the exponential function is a good approximation for $F(\tau)$. At other magnetic field strengths the simple exponential may not necessarily be a good approximation for $F(\tau)$. For the numerical simulations, we repeated the calculation of the $T_2(\tau)$ data set for different pore size distributions where we arbitrarily changed $\Delta$ and $\beta$ to change the shape of the pore size distribution. An exponential dependence of $T_2(\tau)$ is seen to be also an excellent approximation for the numerically calculated results for $T_2(\tau)$ as is evident from the example of FIG. 1c. For this case of a simple exponential dependence of $T_2(\tau)$, the prefactor of the exponential is equivalent to the value of $T_2$ extrapolated to $\tau=0$. Thus the exponential extrapolation of $T_2$ to $\tau=0$ is a measure of the prefactor of the exponential. We therefore expect that the extrapolated value of $T_2$ to $\tau=0$ is proportional to $\Delta$ and this is confirmed by numerical simulations as shown in FIG. 4.

The procedure of estimating $\Delta$ from the $\tau$ dependence of $T_2$ either by prefactor analysis or extrapolation provides a simple estimate of the fluid flow permeability:

$$k \propto \Delta^m \phi^n \quad (28)$$

The proportionality of $T_2(\tau \rightarrow 0)$ to $\Delta$ (and therefore $l_c$) allows one to use $T_2(\tau \rightarrow 0)$ to predict the fluid flow permeability from NMR measurements:

$$k \propto T_2(\tau \rightarrow 0)^m \phi^n \quad (29)$$

It can be shown using pecolation theory [see A. H. Thompson, S. W. Sinton, S. L. Huff, A. J. Katz, R. A. Raschke and G. A. Gist, *J. Appl. Phys.*, 65(8), 3259 (1989)] that $\Delta \propto l_c$ and $l_c$ is the characteristic length obtained from mercury injection. Katz and Thompson [see A. J. Katz and A. H. Thompson, *Phys. Rev. B*, 34, 8179–8181 (1986)] have shown that the absolute permeability k of a porous medium with a broad distribution of pore sizes is related to a characteristic length $l_c$ by:

$$k = \frac{1}{226} l_c^2 \phi^2. \quad (30)$$

$l_c$ in a percolation model represents the largest pore size such that all pores with a diameter $d \geq l_c$ form an infinite connected cluster across the pore space. Therefore m and n in the permeability relations 28 and 29 are approximately equal to 2.0 according to the results of mercury injection experiments. In practice the proportionality constants and exponents can be empirically determined in a calibration experiment.

The theory given to explain the present invention is presented for the sake of illustration only and is not intended to necessarily limit the scope of the claimed invention.

EXPERIMENTAL PROCEDURE

The method of this invention was tested in the laboratory using a nuclear magnetic resonance spectrometer whose functionality can replicate the capabilities of an NMR logging tool instrument. The samples used were sandstone core plugs from various geological formations in North America. For all porous samples we used the following procedure to prepare the samples: The samples were placed in a sealed container and imbibed with water. After imbibing a core plug with water for several hours it was taken out, sealed with Teflon tape and transferred to an NMR glass tube for measurements. In between measurements the samples were kept under water in a sealed container.

Several samples of sandstone rock were used in developing the present invention. The permeability and porosity of these samples was determined by standard methods. In addition on samples obtained from the same batch of rock cores mercury injection experiments were performed to determine a characteristic pore (throat) size $l_c$. Mercury is a non-wetting fluid and under an applied pressure the mercury will first penetrate the largest pores of the medium. For a certain threshold pressure the first continuous path of mercury will be formed between the two ends of the sample and this will be detectable as a jump in the electrical conductivity across the sample. The length $l_c$ can be calculated with the Washburn equation from the threshold pressure at which this first conducting mercury path is established across the sample. The values for permeability, porosity and $l_c$ for the set of sandstone samples used for the NMR experiments are listed in Table 1. These values of permeability and $l_c$ obtained independently from the NMR measurements will have to be compared with the predictions using $T_2(\tau \rightarrow 0)$.

TABLE 1

Sandstone samples and their porosity, permeability and $l_c$ determined independently of the NMR measurements.

| sandstone type | $l_c$ [μm] | porosity [%] | permeability [md] |
| --- | --- | --- | --- |
| Berea | 14.6 | 20.5 | 273 |
| Marsing No. 2 | 118.0 | 29.5 | 54,000 |
| Red Navajo | 23.5 | 23.6 | 1138 |
| Nugget | 10.77 | 10.9 | 4.16 |
| Silver No. 1 | 23.0 | 12.2 | 14.1 |
| Layered Navajo | 28.5 | 25.1 | 883 |
| Marsing No. 1 | 78.6 | 23.9 | 1276 |
| Silver No. 2 | 79.2 | 30.2 | 21,000 |
| Table No. 2 | 91.6 | 24.1 | 3000 |

Figure 5A:
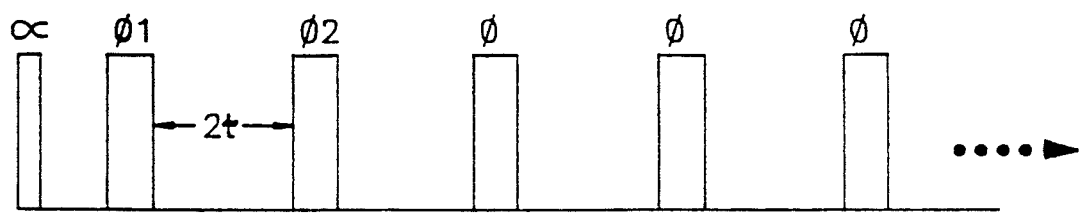
FIG. 5: Schematic diagram of the NMR spin-echo pulse sequence used for the measurement of $T_2$.
Figure 5B:
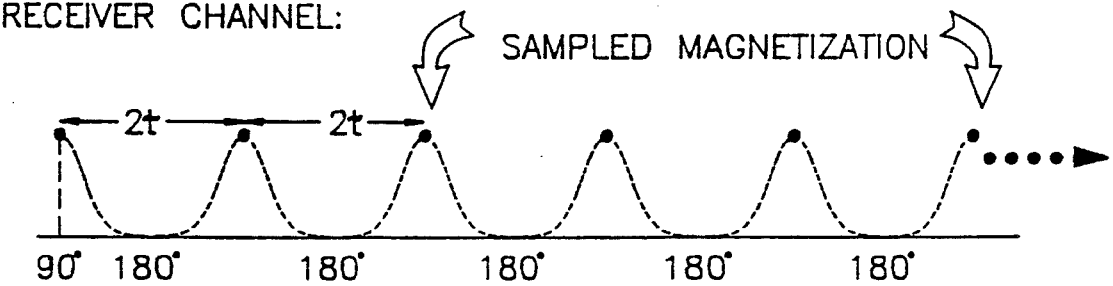

All laboratory NMR experiments were performed at a field strength of 7.05 Tesla corresponding to a Larmor frequency of the hydrogen nucleus of $\nu_L = 300.13$ MHz. The $T_1$ measurements were made with a standard inversion recovery pulse sequence. The $T_1$ measurements were only made for completeness and are not important for the development of this invention. To acquire $T_2$ data we use the Carr-Purcell-Meiboom-Gill (CPMG) pulse sequence which is comprised of an initial 90 radio frequency pulse which tips the longitudinal magnetization into the transverse plane. It is followed a time $\tau/2$ later by a train of 180 pulses with constant pulse spacing $\tau$. At the midpoint between the 180 pulses the nuclear spin magnetization of stationary spins is refocused and a Hahn echo is formed. The echo will be attenuated for spins moving along the orientation of the magnetic field gradients. The magnetization is sampled at the center of the Hahn echoes. This means that for a train of n 180° pulses we acquire n data points. We repeat this experiment for a set of $\tau$ values. This procedure corresponds exactly to one outlined above in the section titled "Method of Invention". FIG. 5 shows a schematic diagram of the pulse sequence.

When measuring the $T_2$ decay with the CPMG sequence as a function of pulse spacing, $T_2$ decreases rapidly for porous samples imbibed with water or oil. By using the CPMG pulse sequence we can ascribe this decay of $T_2$ to the effects of internal magnetic field gradients in the porous sample, which are mainly due to the magnetic susceptibility difference for the fluid imbibing the sample and the matrix. For most samples we recorded the decay of the transverse magnetization with the CPMG sequence for a set of 8–16 values of $\tau$.

DATA ANALYSIS

Figure 6A:
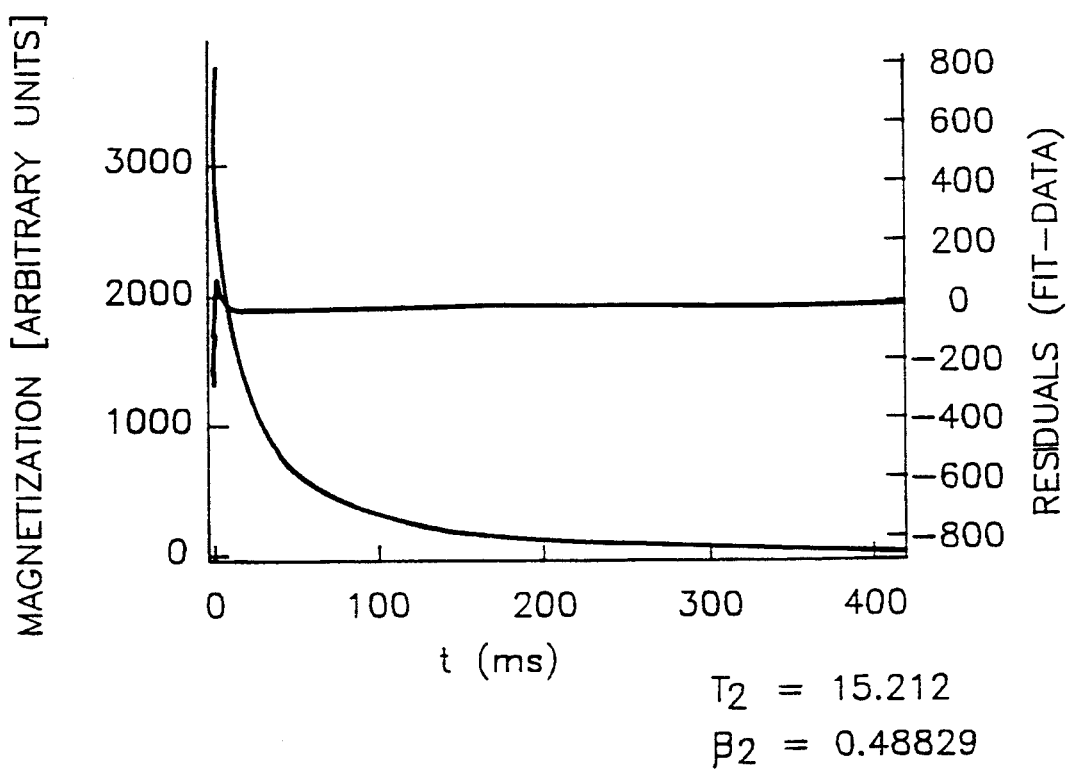
FIG. 6 shows an example of stretched exponential fit to CPMG decay for a water imbibed sandstone sample.
Figure 6B:
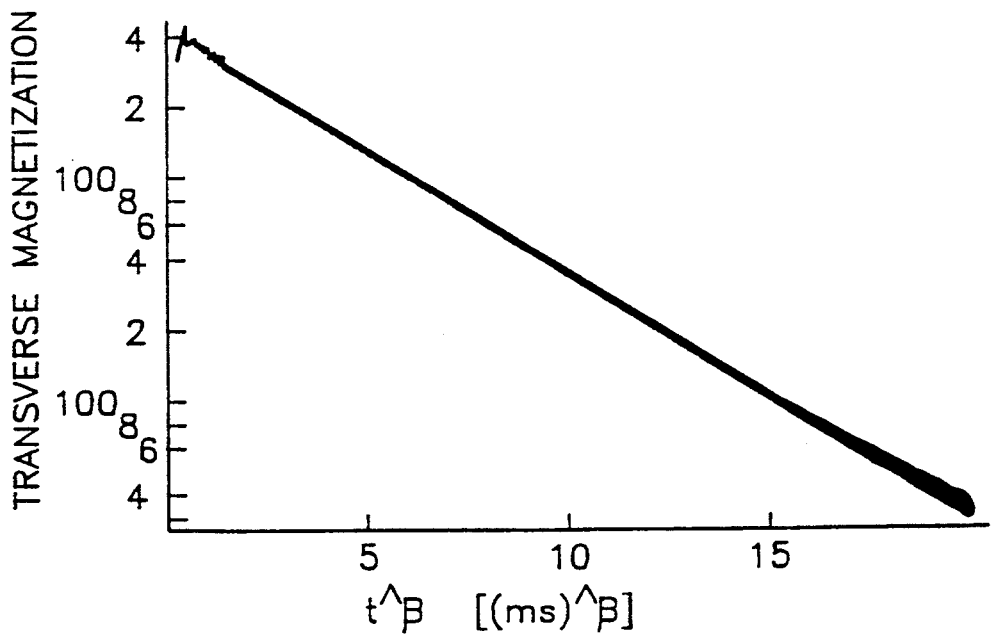

The $T_2$ magnetization decays were fit to a stretched exponential function with a nonlinear least squares fitting procedure. FIG. 6 shows an example of the stretched exponential fit to a $T_2$ CPMG decay curve. The stretched exponential function approximates the experimental data well over 2–3 orders of magnitude as can be seen from FIG. 6b. No data points were discarded before fitting the data to the stretched exponential function.

Figure 7:
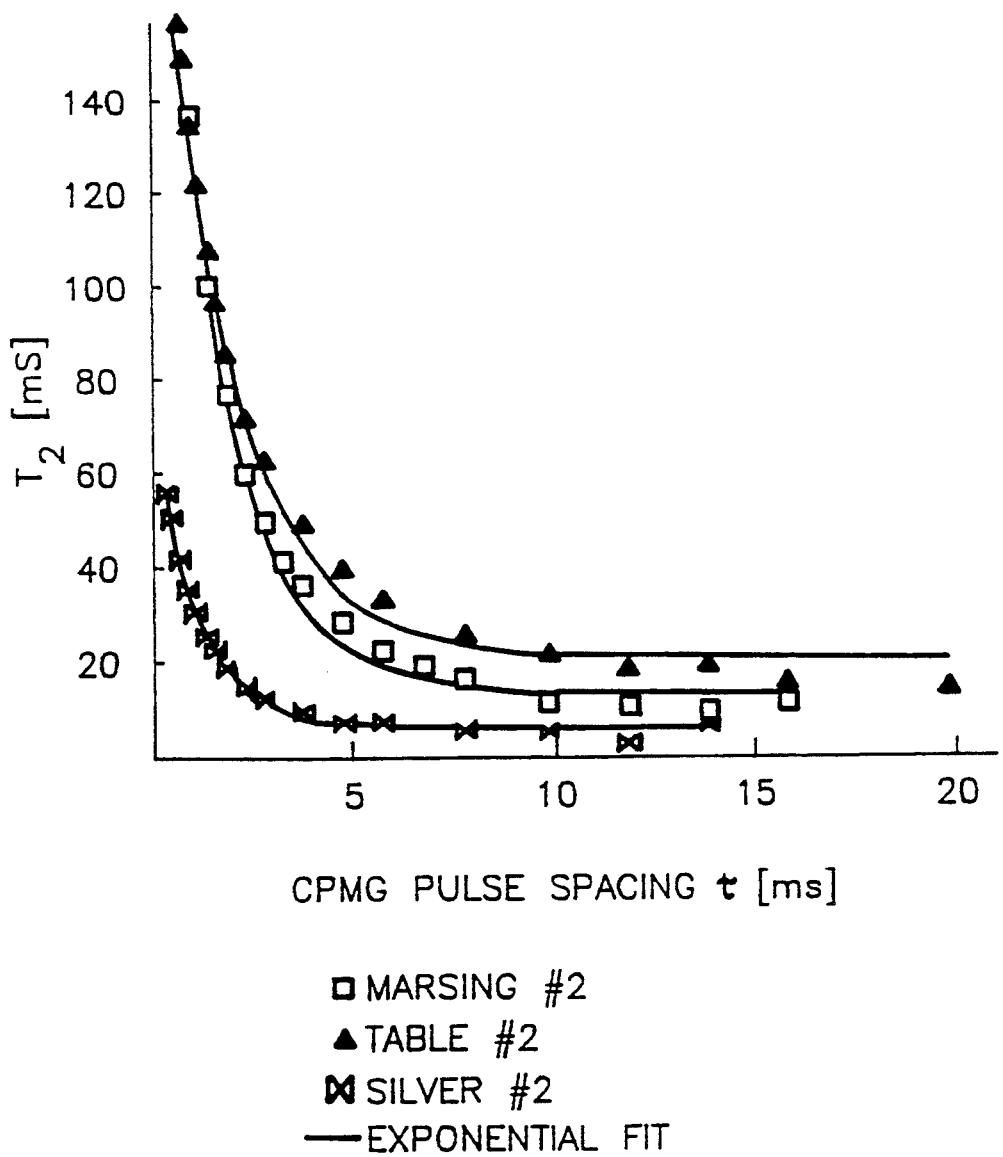
FIG. 7 shows the dependence of $T_2$ on CPMG pulse spacing $\tau$ for a set of sandstone samples. The $T_2$ values can be extrapolated to $T_2(\tau \rightarrow 0)$ with an exponential function.
Figure 8:
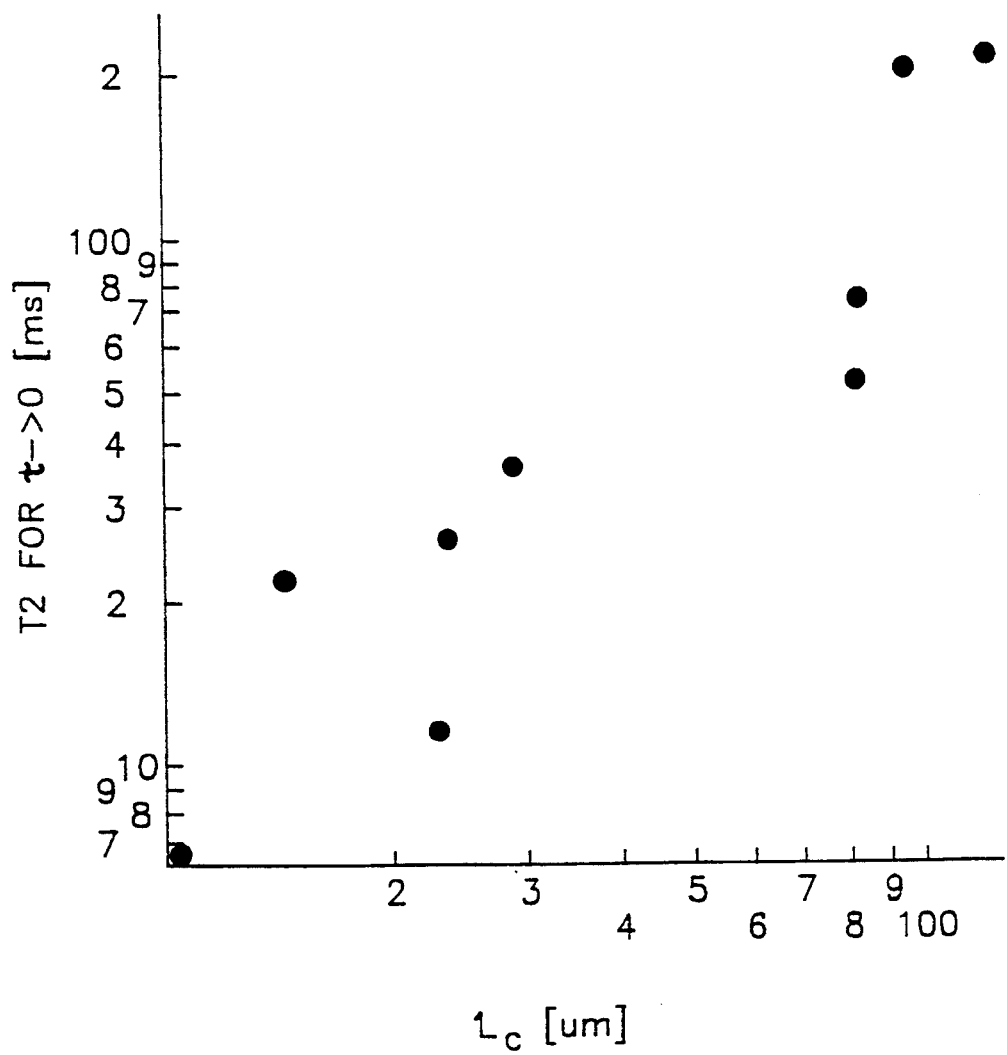
FIG. 8 shows a graph of extrapolated value of $T_2$ versus $l_c$ determined from mercury injection for sandstone rock samples.
Figure 9:
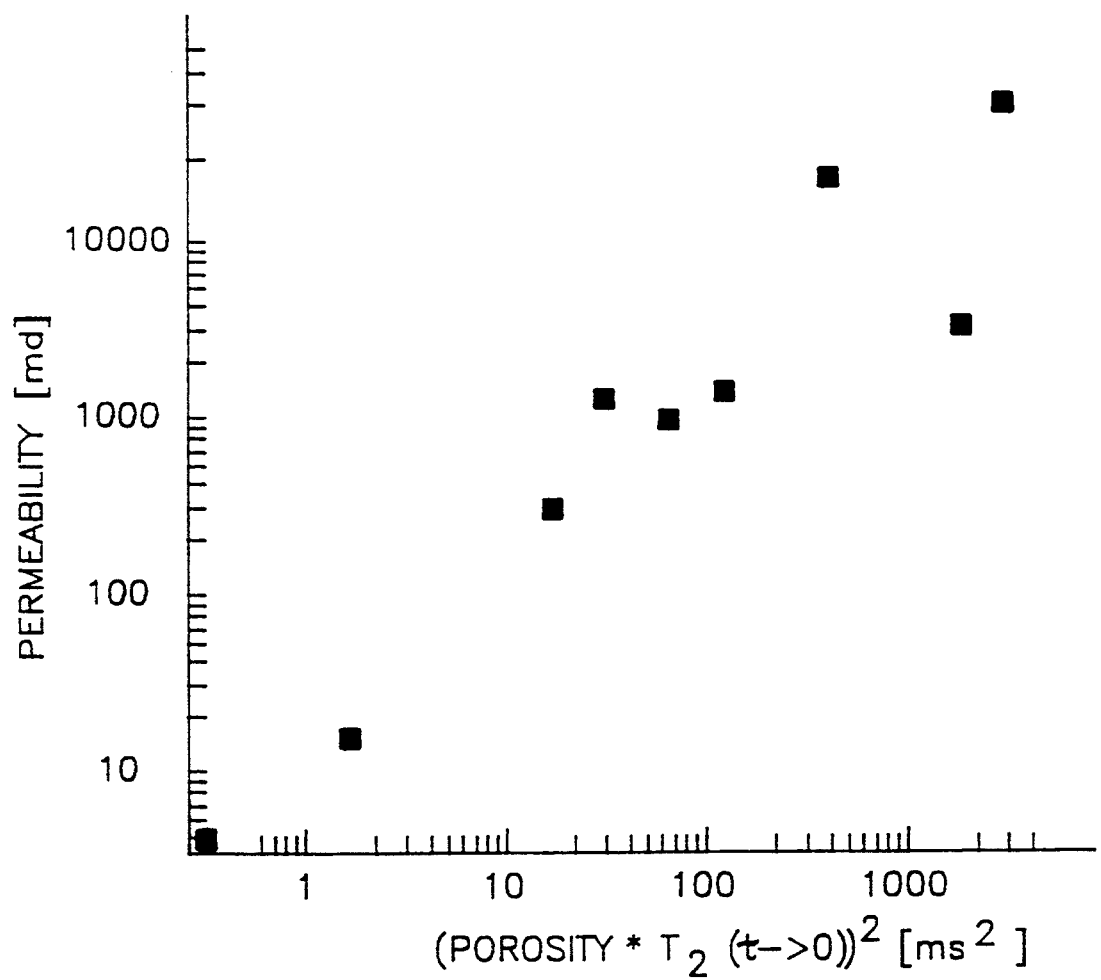
FIG. 9 shows a graph of $T_2(\tau=0) \times \phi$ ($\phi$ is the porosity) versus permeability k for sandstone rock samples.

We acquired for each sample a set of CPMG decay curves by varying $\tau$. The stretched exponential fit yields a value of $T_2$ for each value of $\tau$. The composite set of data point for $T_2(\tau)$ is shown in FIG. 7 for three representative sandstone samples. We fit the resulting set of $T_2(\tau)$ data to a single exponential function. FIG. 7 shows the nonlinear least squares fits as dotted curves. This allows one to extrapolate $T_2(\tau)$ to $\tau=0$. $T_2(\tau \to 0)$ should therefore give a value of the transverse magnetization relaxation time $T_2$ independent of the strength of the internal magnetic field gradients and be proportional to some characteristic length of the pores. FIG. 8 shows a plot of $T_2(\tau=0)$ versus the characteristic pore diameter $l_c$ determined from the threshold pressure for mercury injection via the Washburn equation. Such a relationship is of great value for a rapid order of magnitude determination of permeability based on the above mentioned relationship proposed by Katz and Thompson: $k=1/126\, l_c^2 \phi^2$. And indeed as FIG. 9 shows there exists a correlation between the product of porosity $\phi$ and $T_2(\tau \to 0)$ and the independently determined permeability of the porous rock samples as predicted by the relation $k \propto [T_2(\tau \to 0)]^2 \phi^2$. In this equation the exponent of $T_2(\tau \to 0)$ is predicted to be 2. However the range of the data in FIG. 9 would indicate that the exponent falls into a range of about 1.8 to 2.2. $T_2$ values obtained with the CPMG pulse sequence (which should be the method of choice) are strongly dependent on the pulse spacing $\tau$. Only when the gradient and diffusion induced relaxation is taken into account, do the resulting $T_2(\tau)$ values extrapolated to $\tau=0$ show the discussed correlations with permeability and $l_c$.

For the restricted diffusion analysis of $T_2(\tau)$ we used a nonlinear least squares fitting algorithm to fit the experimental $T_2(\tau)$ data to the expression of equation 22. The prefactor of $\tau$ in the exponent of the exponential is one of the adjustable parameters. $l_{nmr}$ was directly determined from this adjustable fitting parameter obtained from the nonlinear least squares fit.

The present invention takes advantage of the correlations between $T_2$ determined with NMR and a characteristic pore or throat size which determines the fluid flow permeability. This characteristic length $l_c$ can also be determined by mercury injection but mercury injection experiments cannot be carried out in a down-hole environment. For in situ NMR relaxation time measurements in rock formations with an NMR logging tool it is feasible to carry out a $T_2$ measurement described here with the present generation of logging tools and predict the fluid flow permeability using NMR in a manner which is much less time-consuming than other methods known to date.

What is claimed is:

1. A method for determining the permeability of porous media saturated with a liquid using nuclear magnetic resonance (NMR) and comprising:

(a) applying a radiofrequency pulse sequence which after an initial pulse generates successive spin echoes with a train of radio frequency pulses spaced apart by a time interval of length $\tau$ wherein all pulses have a carrier frequency corresponding to the Larmor frequency of the fluid spins filling the pore space of the medium for which the fluid flow permeability is to be determined;

(b) measuring the decay of the transverse magnetization at each of the successive regularly spaced midpoints between the 180 degree pulses where the midpoints coincide with the peak of the spin echoes;

(c) repeating steps a and b at least one more time wherein each repeat of step (a) uses said radio frequency pulse train with a different value of the pulse spacing $\tau$;

(d) determining the transverse relaxation time $T_2(\tau)$, from the transverse magnetization decay for each value of $\tau$, and determining one of a prefactor $\Delta$ and a restricted diffusion length, $l_{nmr}$, from said $T_2(\tau)$:

(e) measuring the porosity of said porous media;

(f) determining the permeability of said media from the porosity and one of the prefactor $\Delta$ and a restricted diffusion length, $l_{nmr}$, from said $T_2(\tau)$:.

2. The method of claim 1 wherein said $T_2(\tau)$ is of a form which includes an exponential function of $\tau$.

3. The method of claim 2 wherein said $T_2(\tau)$ is obtained from an expansion of the exponential functions.

4. The method of claim 2 wherein said $T_2(\tau)$ is a simple exponential function of $\tau$ and said prefactor $\Delta$ is obtained by extrapolation of $T_2(\tau)$ to $\tau \to 0$.

5. The method of claim 1 wherein said porous media is an earth formation and the measurement is performed in a well-bore environment with an NMR logging tool.

6. The method of claim 1 wherein said radio frequency pulse sequence is applied according to the Carr-Purcell-Meiboom-Gill (CPMG) sequence.

7. The method of claim 1 wherein the relaxation time, $T_2$ is obtained from the transverse magnetization decay in step (d) by relating the transverse magnetization to time by a stretched exponential function.

8. The method of claim 1 wherein said permeability of step (f) is determined from the product of the porosity and restricted diffusion length $l_{nmr}$.

9. The method of claim 8 wherein said porosity and restricted diffusion length $l_{nmr}$ are each raised to a power.

10. The method of claim 8 wherein $l_{nmr}$ is determined using a restricted diffusion model.

11. The method of claim 1 wherein said permeability of step (f) is determined from the product of the porosity and the prefactor $\Delta$.

12. The method of claim 11 wherein said porosity and the prefactor $\Delta$ are each raised to a power.

13. The method of claim 11 wherein prefactor $\Delta$ is determined as prefactor of the observed $T_2(\tau)$ dependence.

14. The method of claim 4 wherein said permeability of step (f) is obtained from the product of the porosity and the extrapolated transverse relaxation time, $T_2$ at $\tau=0$.

15. The method of claim 14 wherein said porosity and the extrapolated transverse relaxation time, $T_2$ at $\tau=0$ are each raised to a power.

16. The method of claim 9 wherein said powers are between about 1.8 and 2.2.

17. The method of claim 12 wherein said powers are between about 1.8 and 2.2.

18. The method of claim 15 wherein said powers are between about 1.8 and 2.2.

19. The method of claim 16 wherein said powers are 2.

20. The method of claim 17 wherein said powers are 2.

21. The method of claim 18 wherein said powers are 2.

* * * * *